United States Patent
Fei et al.

(10) Patent No.: US 9,022,953 B2
(45) Date of Patent: May 5, 2015

(54) LANCET ANALYTE SENSORS AND METHODS OF MANUFACTURING

(75) Inventors: Jiangfeng Fei, Sleepy Hollow, NY (US); Raeann Gifford, Cortlandt Manor, NY (US); Serban Peteu, East Lansing, MI (US); Paul M. Ripley, Nanuet, NY (US); Hoi-Cheong Steve Sun, Mount Kisco, NY (US); Mu Wu, Hopewell Junction, NY (US)

(73) Assignee: Bayer Healthcare LLC, Whippany, NJ (US)

( * ) Notice: Subject to any disclaimer, the term of this patent is extended or adjusted under 35 U.S.C. 154(b) by 891 days.

(21) Appl. No.: 13/119,344

(22) PCT Filed: Sep. 17, 2009

(86) PCT No.: PCT/US2009/057253
§ 371 (c)(1),
(2), (4) Date: Mar. 16, 2011

(87) PCT Pub. No.: WO2010/033660
PCT Pub. Date: Mar. 25, 2010

(65) Prior Publication Data
US 2011/0172559 A1  Jul. 14, 2011

Related U.S. Application Data

(60) Provisional application No. 61/098,714, filed on Sep. 19, 2008.

(51) Int. Cl.
*A61B 5/00* (2006.01)
*B65D 81/00* (2006.01)
(Continued)

(52) U.S. Cl.
CPC ........... *A61B 5/1411* (2013.01); *A61B 5/14514* (2013.01); *A61B 5/14532* (2013.01);
(Continued)

(58) Field of Classification Search
CPC ........ A61B 5/151; A61B 5/157; A61B 5/145; A61B 5/05
USPC ................. 600/583, 352, 347, 345, 573, 584; 435/7.1; 257/414; 436/180, 148, 169, 436/177; 422/504; 73/863.11, 863.12, 73/864.52, 864.61
See application file for complete search history.

(56) References Cited

U.S. PATENT DOCUMENTS

| 4,326,927 A | 4/1982 | Stetter et al. |
| 4,596,741 A | 6/1986 | Endou et al. |

(Continued)

FOREIGN PATENT DOCUMENTS

| WO | WO 2006/057722 | 6/2006 |
| WO | WO 2009/100082 | 8/2009 |

(Continued)

OTHER PUBLICATIONS

Isao Karube et al., "Integrated Microbiosensors for Medical Use", Dec. 1, 1989, Annals of New York Academy of Sciences, vol. 542, No. 9, pp. 470-479.

(Continued)

*Primary Examiner* — Brian Szmal
(74) *Attorney, Agent, or Firm* — Dugan & Dugan, PC

(57) ABSTRACT

In some aspects, an analyte sensor is provided for obtaining and detecting an analyte concentration level in a bio-fluid sample. The analyte sensor has a sensor body including a semiconductor material, an active region coupled to the sensor body, and a lancet provided on the analyte sensor. The conductor may include a fiber having a core of a conductive material and a semiconductor cladding surrounding the core. Numerous other aspects are provided.

21 Claims, 9 Drawing Sheets

(51) Int. Cl.
*A61B 5/15* (2006.01)
*A61B 5/145* (2006.01)
*A61B 5/1486* (2006.01)
*A61B 5/151* (2006.01)
*A61B 5/157* (2006.01)

(52) U.S. Cl.
CPC ....... *A61B5/14865* (2013.01); *A61B 5/150022* (2013.01); *A61B 5/150213* (2013.01); *A61B 5/150282* (2013.01); *A61B 5/150396* (2013.01); *A61B 5/150427* (2013.01); *A61B 5/150511* (2013.01); *A61B 5/150984* (2013.01); *A61B 5/15105* (2013.01); *A61B 5/15119* (2013.01); *A61B 5/15123* (2013.01); *A61B 5/157* (2013.01); *A61B 5/685* (2013.01)

(56) References Cited

U.S. PATENT DOCUMENTS

| | | | |
|---|---|---|---|
| 5,431,800 A | | 7/1995 | Kirchhoff et al. |
| 5,476,776 A | | 12/1995 | Wilkins |
| 5,611,900 A | | 3/1997 | Worden et al. |
| 5,627,922 A | | 5/1997 | Kopelman et al. |
| 5,700,695 A | * | 12/1997 | Yassinzadeh et al. ........ 436/180 |
| 5,777,372 A | | 7/1998 | Kobashi |
| 5,866,353 A | | 2/1999 | Berneth |
| 6,218,661 B1 | | 4/2001 | Schroeder et al. |
| 6,521,109 B1 | | 2/2003 | Bartic et al. |
| 6,743,635 B2 | | 6/2004 | Neel et al. |
| 7,074,519 B2 | | 7/2006 | Kuhr et al. |
| 7,951,632 B1 | | 5/2011 | Quick et al. |
| 8,202,697 B2 | * | 6/2012 | Holmes .......................... 435/7.1 |
| 2002/0137998 A1 | * | 9/2002 | Smart et al. .................... 600/347 |
| 2002/0168290 A1 | | 11/2002 | Yuzhakov et al. |
| 2002/0177763 A1 | * | 11/2002 | Burns et al. .................... 600/345 |
| 2003/0088166 A1 | | 5/2003 | Say et al. |
| 2003/0212344 A1 | * | 11/2003 | Yuzhakov et al. ............. 600/583 |
| 2003/0217918 A1 | | 11/2003 | Davies et al. |
| 2004/0002682 A1 | | 1/2004 | Kovelman et al. |
| 2004/0039303 A1 | | 2/2004 | Wurster et al. |
| 2004/0094432 A1 | | 5/2004 | Neel et al. |
| 2004/0136866 A1 | | 7/2004 | Pontis et al. |
| 2004/0146863 A1 | | 7/2004 | Pisharody et al. |
| 2004/0200721 A1 | | 10/2004 | Bhullar et al. |
| 2004/0254546 A1 | | 12/2004 | Lefebvre |
| 2005/0183953 A1 | | 8/2005 | Su et al. |
| 2005/0238537 A1 | | 10/2005 | Say et al. |
| 2005/0261606 A1 | * | 11/2005 | Sohrab ........................... 600/573 |
| 2005/0279647 A1 | | 12/2005 | Beaty |
| 2005/0287065 A1 | | 12/2005 | Suddarth et al. |
| 2006/0113187 A1 | | 6/2006 | Deng et al. |
| 2006/0211933 A1 | | 9/2006 | Zimmermann et al. |
| 2007/0087492 A1 | | 4/2007 | Yamanaka |
| 2007/0096164 A1 | | 5/2007 | Peters et al. |
| 2008/0027302 A1 | * | 1/2008 | Buse et al. ..................... 600/347 |
| 2008/0167578 A1 | * | 7/2008 | Bryer et al. .................... 600/583 |
| 2008/0197024 A1 | | 8/2008 | Simpson et al. |
| 2009/0018411 A1 | * | 1/2009 | Mace et al. ..................... 600/309 |
| 2010/0270150 A1 | * | 10/2010 | Wang et al. ............. 204/403.01 |
| 2010/0274181 A1 | * | 10/2010 | Wang et al. ..................... 604/66 |
| 2010/0298679 A1 | | 11/2010 | Wu et al. |
| 2011/0180405 A1 | * | 7/2011 | Chinnayelka et al. ... 204/403.15 |

FOREIGN PATENT DOCUMENTS

| | | |
|---|---|---|
| WO | WO 2010/033660 | 3/2010 |
| WO | WO 2010/033668 | 3/2010 |
| WO | WO 2010/033741 | 3/2010 |
| WO | WO 2010/033748 | 3/2010 |

OTHER PUBLICATIONS

International Preliminary Report on Patentability and Written Opinion of International Application No. PCT/US2009/032991 mailed Aug. 19, 2010.
International Search Report and Written Opinion of related International Application No. PCT/US2009/057264 mailed Nov. 10, 2009.
International Preliminary Report on Patentability of related International Application No. PCT/US2009/057264 mailed Mar. 31, 2011.
International Search Report and Written Opinion of International Application No. PCT/US2009/057372 mailed Nov. 13, 2009.
International Preliminary Report on Patentability of related International Application No. PCT/US09/057382 mailed Mar. 31, 2011.
International Search Report and Written Opinion of International Application No. PCT/US09/057382 mailed Feb. 1, 2010.
International Preliminary Report on Patentability and Written Opinion of related International Application No. PCT/US2009/057372 mailed Mar. 31, 2011.
International Preliminary Report on Patentability Search Report and Written Opinion of related International Application No. PCT/US2009/057253 mailed Mar. 31, 2011.
International Search Report and Written Opinion of International Application No. PCT/US2009/032991 mailed Aug. 6, 2009.
Communication pursuant to Rules 161(2) and 162 EPC of related European Application No. 09815226.7 May 12, 2011.
Communication pursuant to Rules 161(2) and 162 EPC of related European Application No. 09815166.5 May 13, 2011.
Communication pursuant to Rules 161(2) and 162 EPC of related European Application No. 09815223.4 May 12, 2011.
Communication pursuant to Rules 161(2) and 162 EPC of related European Application No. 09815172.3 May 25, 2011.
Singh et al., "SiC-C Fiber Electrode for Biological Sensing", Feb. 22, 2007, Materials Science and Engineering C, Elsevier Science S.A., vol. 27, No. 3, pp. 551-557.
International Search Report and Written Opinion of related International Application No. PCT/US2009/057253 mailed Nov. 2, 2009.
Extended Search Report of related European Application No. 09815223.4 dated Oct. 2, 2012.
Communication pursuant to Rules 70(2) and 70a(2) EPC of related European Application No. 09815223.4 dated Oct. 19, 2012.
Schackleford et al., CRC Materials Science and Engineering Handbook, 3rd ed., 2000, Table 154.
Extended Search Report of related European Application No. 09815166.5 dated Oct. 22, 2012.
Extended Search Report of related European Application No. 09815226.7 May 9, 2014.
Sengupta, D.K., et al. "Laser Conversion of Electrical Properties for Silicon Carbide Device Applications", Jour. of Laser Applications, vol. 13, Jan. 1, 2011, pp. 26-31.
Wang et al., "Miniaturized Glucose Sensors Based on Electrochemical Codeposition of Rhodium and Glucose Oxidase onto Carbon-Fiber Electrodes, 1992, The American Chemical Society," vol. 64, pp. 456-459.

* cited by examiner

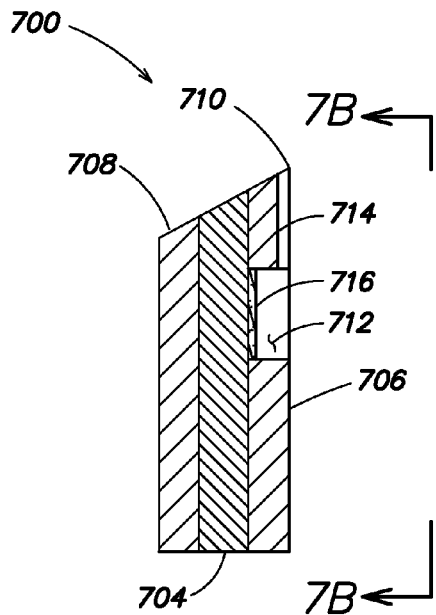
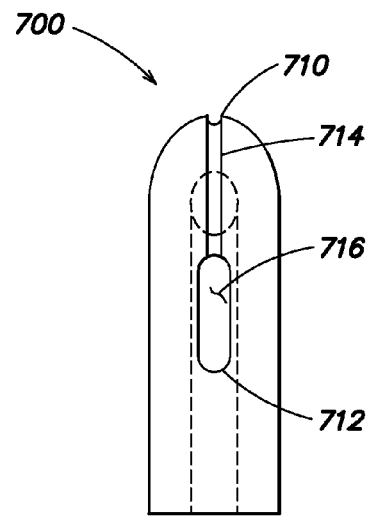
FIG. 7A    FIG. 7B
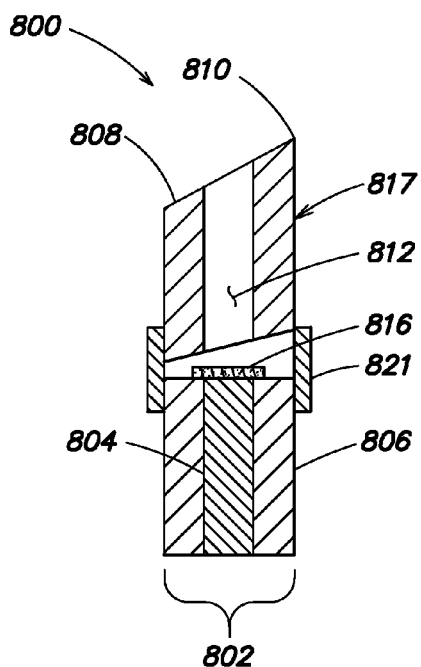
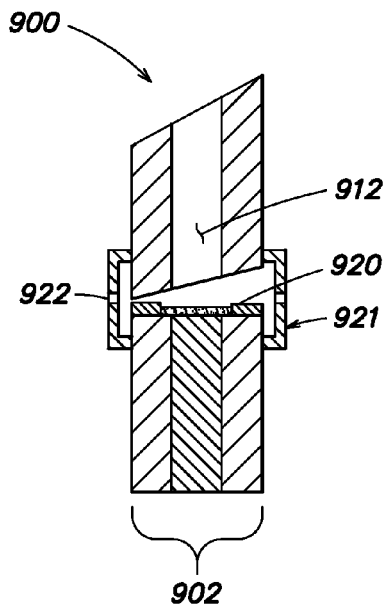
FIG. 8    FIG. 9

LANCET ANALYTE SENSORS AND METHODS OF MANUFACTURING

RELATED APPLICATIONS

The present application claims priority to U.S. Provisional Patent Application No. 61/098,714 filed Sep. 19, 2008, and entitled "LANCET ANALYTE SENSORS AND METHODS OF MANUFACTURING" which is hereby incorporated herein by reference in its entirety for all purposes.

FIELD OF THE INVENTION

The present invention relates to electrochemical analyte sensors that may be used to detect an analyte concentration level in a bio-fluid sample taken from a patient.

BACKGROUND OF THE INVENTION

The monitoring of analyte concentration levels in a bio-fluid may be an important part of health diagnostics. For example, an electrochemical analyte sensor may be employed for the monitoring of a patient's blood glucose level as part of diabetes treatment and care.

An electrochemical analyte sensor may be employed discretely ('discrete monitoring'), for instance, by detecting an analyte concentration level in a single sample of blood or other interstitial fluid obtained from the patient by a lancet (e.g., by a pin-prick or needle). Optionally, the analyte sensor may be employed continuously ('continuous monitoring'), by implanting a sensor in the patient for a duration of time. In discrete monitoring, there may be a separation between the sample collection process and the measurement of the analyte concentration level. Typically, after a bio-fluid sample has been obtained from the patient, such as by the use of a lancet, the sample may then be transferred to a medium (e.g., a test strip or a detector) for measurement of the sample's analyte concentration level.

Conventional lancets, if too large, may cause undue pain and discomfort to the patient when inserted. Further, because conventional electrochemical analyte sensors may be of relatively low sensitivity and transfer of a bio-fluid sample to the sensor may be relatively inefficient, a relatively large sample volume may be required in order to yield an accurate measurement of the analyte concentration level. In such instances, if the sample provided is too small, the sensor may be provided with an insufficient sample volume for an accurate reading. Thus, additional bio-fluid may need to be drawn from the patient. Consequently, lancet insertion may need to be repeated, causing further patient pain and discomfort.

It would therefore be beneficial to provide an analyte sensor adapted for bio-fluid analyte monitoring that is minimally invasive during sample collection, and yet consistently and readily provides for accurate analyte concentration level measurements from the obtained bio-fluid sample.

SUMMARY OF THE INVENTION

In an aspect, the present invention provides an analyte sensor, including a sensor body comprised of a semiconductor material; an active region coupled to the sensor body; and a lancet formed on an end of the analyte sensor.

In another aspect, the present invention provides an analyte sensor for detecting an analyte concentration level in a bio-fluid sample, including a core comprised of a conductive material; a cladding comprised of a semiconductor material surrounding the core; a cavity formed proximate to the core, and an active region provided within the cavity.

In another aspect, the present invention provides an analyte sensor for detecting an analyte concentration level in a bio-fluid sample, including a fiber comprised of a semiconductor material; an active region in contact with the fiber, and a lancet formed on the analyte sensor.

In another aspect, the present invention provides a testing apparatus, including an analyte sensor having a sensor body comprised of a semiconductor material; an active region coupled to the sensor body; and a lancet formed on an end of the analyte sensor.

In a method aspect, the present invention provides a method of manufacturing an analyte sensor, including providing a fiber comprised of a semiconductor material; forming a cavity proximate to the fiber, forming an active region in the cavity, and forming lancet on the analyte sensor.

Other features and aspects of the present invention will become more fully apparent from the following detailed description, the appended claims and the accompanying drawings.

BRIEF DESCRIPTION OF THE DRAWINGS

FIG. 7A is a cross-sectional view of additional exemplary embodiment of an analyte sensor according to the present invention.

FIG. 7B is a frontal view of the exemplary embodiment of the analyte sensor of FIG. 7A.

FIGS. 8-9 are cross-sectional views of additional exemplary embodiments of analyte sensors according to the present invention.

DETAILED DESCRIPTION

Figure 1A:
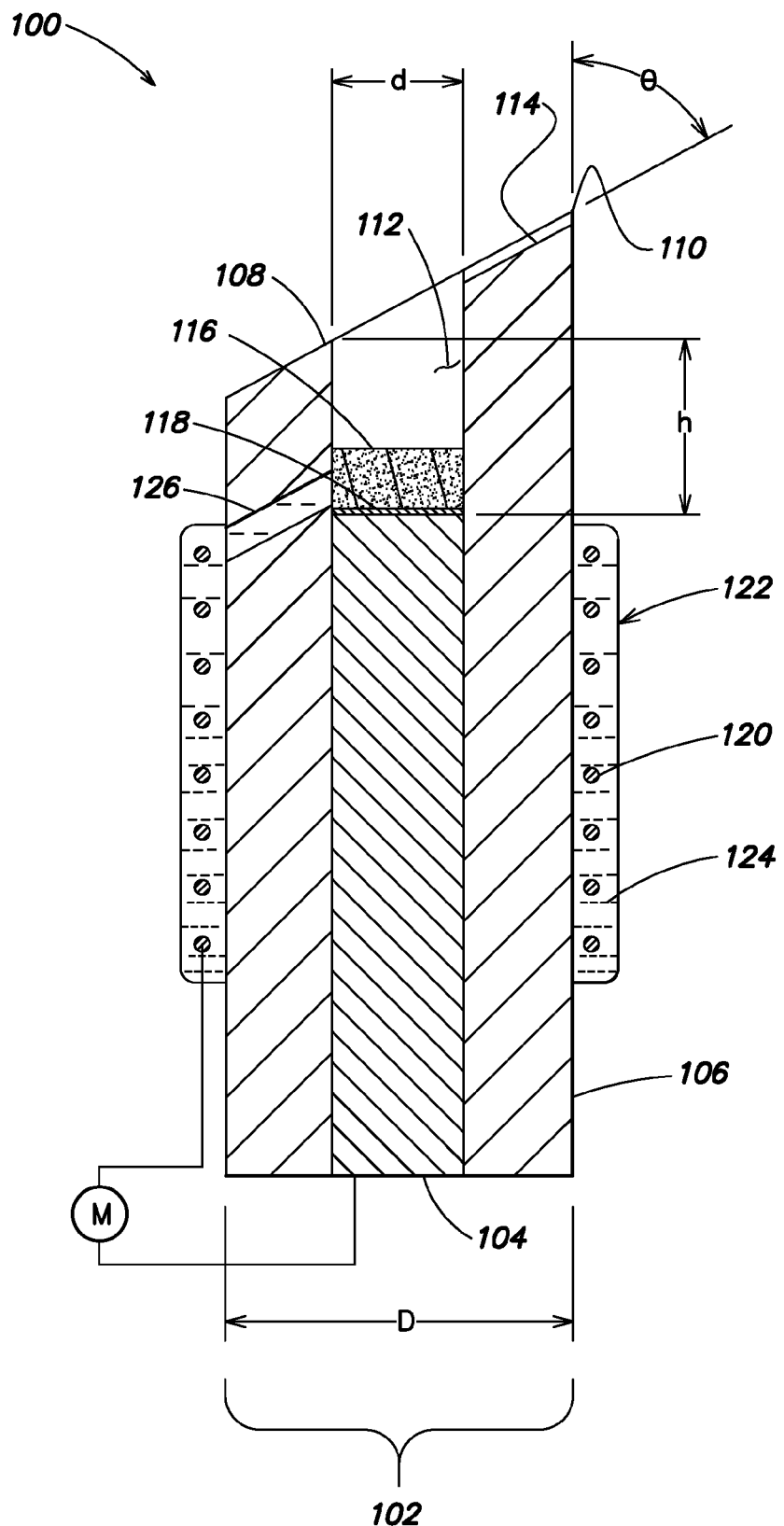
FIG. 1A is a cross-sectional view of an exemplary embodiment of an analyte sensor provided according to the present invention.

According to a first aspect of the present invention, a lancet analyte sensor is provided that integrates the functions of a lancet and an analyte sensor into a single device. In this manner, the processes of sample collection and analyte detection may be performed without the need to transfer the sample to a transfer medium, such as an analyte sensor strip or an external detection or testing device.

An exemplary lancet analyte sensor (hereinafter otherwise referred to as an "analyte sensor" or simply a "sensor") may include a sensor body comprised of a semiconductor material. The sensor body in some embodiments may include a core including a conductive material and a cladding. In some embodiments, the conductive core of the analyte sensor may comprise carbon (e.g., graphite) and the semiconductor cladding may comprise silicon carbide.

In one or more embodiments, a lancet may be formed on the analyte sensor. Lancet is defined herein as a sharpened area or point that is provided on an end of the lancet analyte sensor. For example, in some embodiments, a cladding of the conductor may be cleaved at an angle at one end to provide a lancet for insertion. Optionally, the lancet may be a separate member and may be otherwise coupled to the sensor body, such as to the cladding for example.

Further, the analyte sensor may include a cavity located proximate to the sensor body (e.g., proximate the core) for accepting the bio-fluid sample. The term "cavity" as defined herein is a hollow, indented, or concave area having walls adapted to contain and confine the bio-fluid sample. In some embodiments, the cavity may be at least partially surrounded by the cladding whereby the walls of the cavity are formed by the cladding material (e.g., by an inner surface of the cladding). In other embodiments, the cavity is at least partially formed by walls of a lancet member connected to the sensor body. In further embodiments, the cavity may be formed in a peripheral side wall of the sensor body. Furthermore, the cavity may be provided with an active region which may be coupled to the core and/or cladding and may be adapted to generate an electrical current which may be proportional to an analyte concentration level.

The diameter of the lancet analyte sensor may be smaller than conventional lancets, such that the lancet analyte sensor may be inserted into a patient without causing much, if any, discomfort. For example, the sensor body may have an outside diameter of about 150 microns or less, about 100 microns or less, about 75 microns or less, or even about 50 microns or less. Upon insertion, a small volume of the bio-fluid sample (e.g., blood, interstitial fluid, or other body fluid) may be guided into the cavity of the sensor, such as by capillary action for example. The required sample volume for an accurate reading may constitute less than about 0.4 microliters, less than about 0.3 microliters, or even less than about 0.2 microliters, for example. In some embodiments, the required sample volume may be less than about 0.1 microliters, or even less than about 0.05 microliters, for example.

The active region of the lancet analyte sensor may include one or more catalytic agents and/or reagents adapted to react and convert an analyte in a received bio-fluid sample into reaction products from which an electrical current may be generated. The resulting electrical current may flow in the sensor body. For example, the current may flow in the core and/or the cladding. Thus, in some embodiments, the conductive material of the core and/or semiconductor material of the cladding may form at least a portion of a working electrode. The electrical current may then be detected, such as by a measurement or testing device (e.g., an ammeter) connected to the working electrode, thereby enabling a determination of an analyte concentration level in the bio-fluid sample.

In operation, the electrical current may have a magnitude, which may be correlated with the concentration of the analyte in the bio-fluid sample, for example. These and other embodiments of the analyte sensors of the present invention are described below with reference to FIGS. 1A-10.

FIG. 1A is a cross-sectional side view of an exemplary embodiment of a lancet analyte sensor 100 provided according to the present invention. The analyte sensor 100 may include a sensor body 102, which may be approximately cylindrical in shape. The sensor body 102 may further comprise a semiconductor material. In particular, the body 102 may include a core 104 comprised of a conductive material. The core 104 may be at least partially surrounded by a cladding 106, which may be comprised of the semiconductor material. In the exemplary embodiment shown, the cladding 106 may include an annular shape and may fully surround the core 104, which may comprise the shape of a cylindrical rod. Both the core 104, which may be comprised of a conductive material, and the cladding 106, which may be comprised of semiconductor material, may convey electrical current, albeit the semiconductor material may have a higher resistivity as compared to the core 104 and may carry, therefore, less current than the core 104. In some embodiments, the core 104 may comprise carbon (e.g. graphite) and the cladding 106 may comprise silicon carbide (SiC).

In some embodiments, the sensor body may be provided in the form of a fiber (e.g., a SiC/C fiber). SiC/C fibers having a suitable SiC cladding and carbon core are manufactured by Specialty Materials Inc. of Lowell, Mass., for example. However, the conductive material of the core 104 may comprise other conductive materials including graphite, noble metals (e.g., platinum, tantalum, gold or silver) or other conductive metals (e.g., aluminum or copper). The cladding 106 may comprise other semiconductor materials including Group IV elements such as silicon and germanium, Group IV compounds such as silicon germanide (SiGe), and Group III-V compounds such as gallium arsenide (GaAs) and indium phosphide (InP), among others.

Furthermore, in some embodiments the sensor body 102 may have a total diameter D (including the core 104 and cladding 106) of about 150 microns or less, about 100 microns or less, about 75 microns or less, or even about 50 microns or less. The total diameter D may range between about 50 microns and about 150 microns in some embodiments (although larger or smaller sizes may also be used). The core 104 may have a diameter d between about 10 microns and about 100 microns, or even between about 20 microns and about 40 microns. In some embodiments, a diameter d of about 30 microns may be used, although other dimensions may also be used. In embodiments in which a SiC cladding 106 is used, the sensor body 102 may be fabricated and machined (e.g., by a laser) easily at small diameters (e.g., less than 150 microns). In addition, the high tensile strength of SiC of between about 3450 MPa to 5865 MPa may provide desirable strength to the sensor body 102. Moreover, even at this reduced diameter, the sensor body 102 having a SiC cladding 106 may have a modulus sufficient to provide flexibility for bending or deformation and ultimate strength sufficient to prevent breakage during insertion.

The sensor body 102 may be cleaved at an angle at one end 108 (the 'cleaved end') to form a lancet 110 which can be readily inserted into a patient to obtain a bio-fluid sample (e.g., blood, interstitial fluid, or other bodily fluid). Exemplary cleave angles θ range from about 25 degrees to about 50 degrees, and are preferably about 35 degrees, although other angles may be used. The cleaved angle may be readily cut by a laser, which may provide a smooth surface finish.

Located proximate to the cleaved end 108 and the core 104 of the sensor body 102, a cavity 112 may be provided. The cavity 112 may be formed, for example, by removing a portion of the material forming the core 104 to produce a hollowed out area. In some embodiments, the cavity 112 may have a diameter equivalent to the diameter d of the core 104 (e.g., about 10 to about 100 microns). However, the diameter of the cavity may be larger or smaller than the core as well, and may be of irregular shape, such as oval or elongated (in a cross sectional view). The depth h of the cavity 112 may be between about 0.5 mm and about 5 mm, for example. Other cavity dimensions may be used.

Any suitable technique may be used to remove the core material to form the cavity 112, such as machining, thermal oxidation (using a torch or laser), etching, plasma or corona discharge machining, or the like. In some embodiments, the melting point of the conductive core 104 may be below that of the semiconductor cladding 106 thereby enabling preferential removal of core material without simultaneous removal of cladding material.

In some embodiments, a channel 114 may be formed in the cladding 106 at the cleaved end 108 proximate to the lancet 110 such as by deep reactive etching, for example. The channel 114 may be coupled directly to the cavity 112. Accordingly, during usage, the channel 114 may be in fluid communication with the cavity 112 such that during an insertion of the lancet 110 into a patient, at least a portion of the sample bio-fluid contacting an area located around the lancet 110 may be drawn, such as by capillary action, into the channel 114 and/or may otherwise be guided into the cavity 112. In some embodiments, the channel 114 may have a width of about 10 microns to about 100 microns, and a depth of between about 10 microns to about 100 microns, although other dimensions may be used. The channel may be square or rectangular in cross section, and may have rounded corners, for example.

Figure 1B:
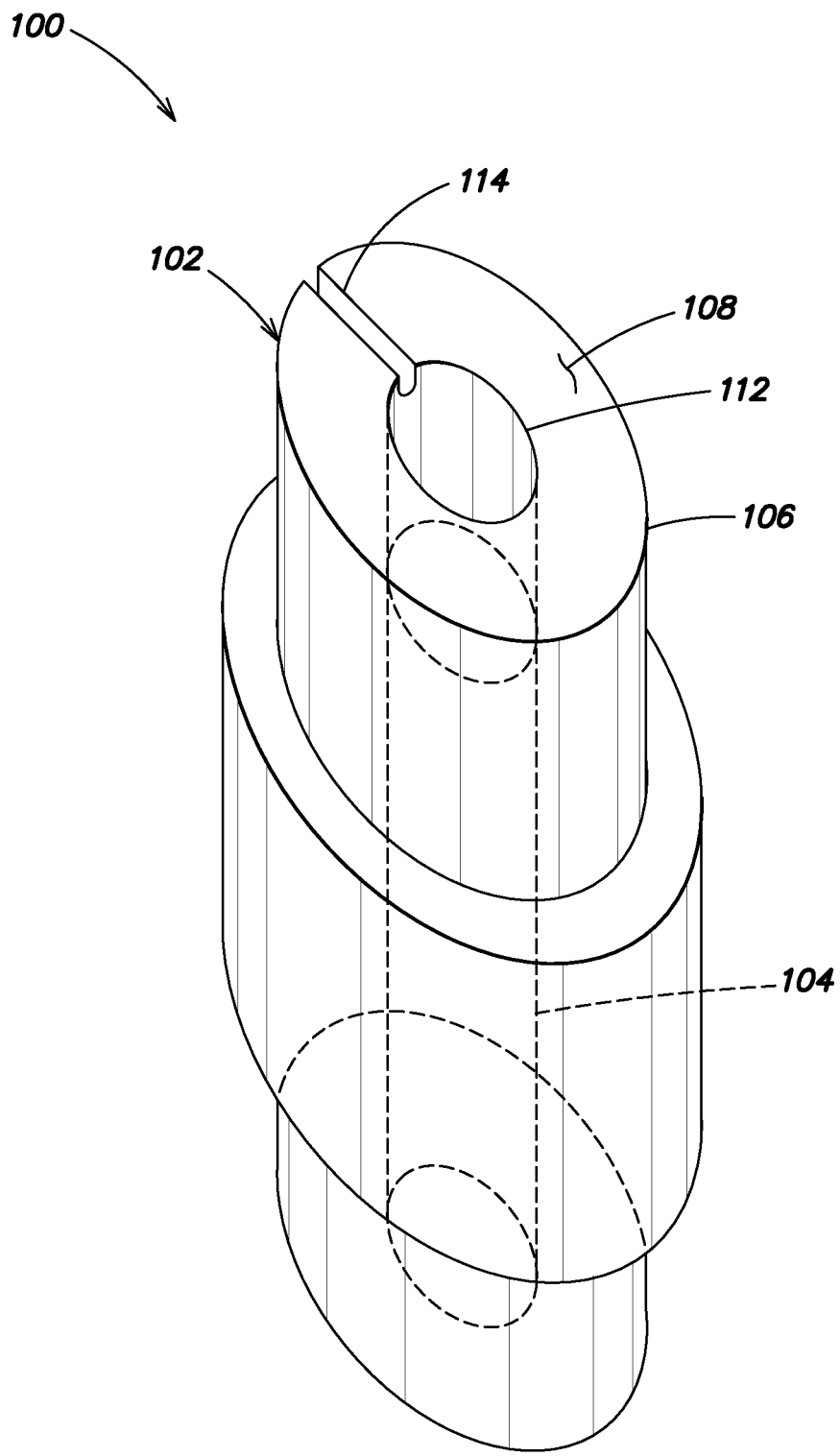
FIG. 1B is a perspective view of the analyte sensor according to the exemplary embodiment shown in FIG. 1A.

A perspective view of the sensor body 102 including the core 104 and cladding 106 and the cleaved end 108 of the sensor 100 is depicted in FIG. 1B. As illustrated, the channel 114 may be formed into the cleaved end 108 and intersects with the cavity 112. More than one channel 114 may also be used. It is noted, however, that the small diameter of the cavity 112 may be sufficient by itself to induce capillary action for drawing a bio-sample into the cavity 112 without the aid of the channel 114. Optionally a vent hole (not shown) may be provided in a side wall of the sensor body. In some embodiments, a sufficient sample for purposes of detecting an analyte concentration level may have a volume of less than about 3 microliters, less than about 2 microliters, less than about 1 microliters, or even less than about 0.5 microliters. In further exemplary embodiments, the relatively small diameter of the sensor body may provide for a sufficient sample volume being less than about 0.4 microliters, less than about 0.3 microliters, less than about 0.2 microliters, less than about 0.1 microliters, or even less than about 0.05 microliters, for example. A sufficient sample volume may, in some embodiments, range between about 0.05 microliters to about 3 microliters. Other sample volumes may also be employed. The combination of the small diameter of the sensor body 102 and the capillary action into the cavity 112 may reduce or eliminate much of the pain and discomfort associated with bio-fluid sample collection.

Figure 3:
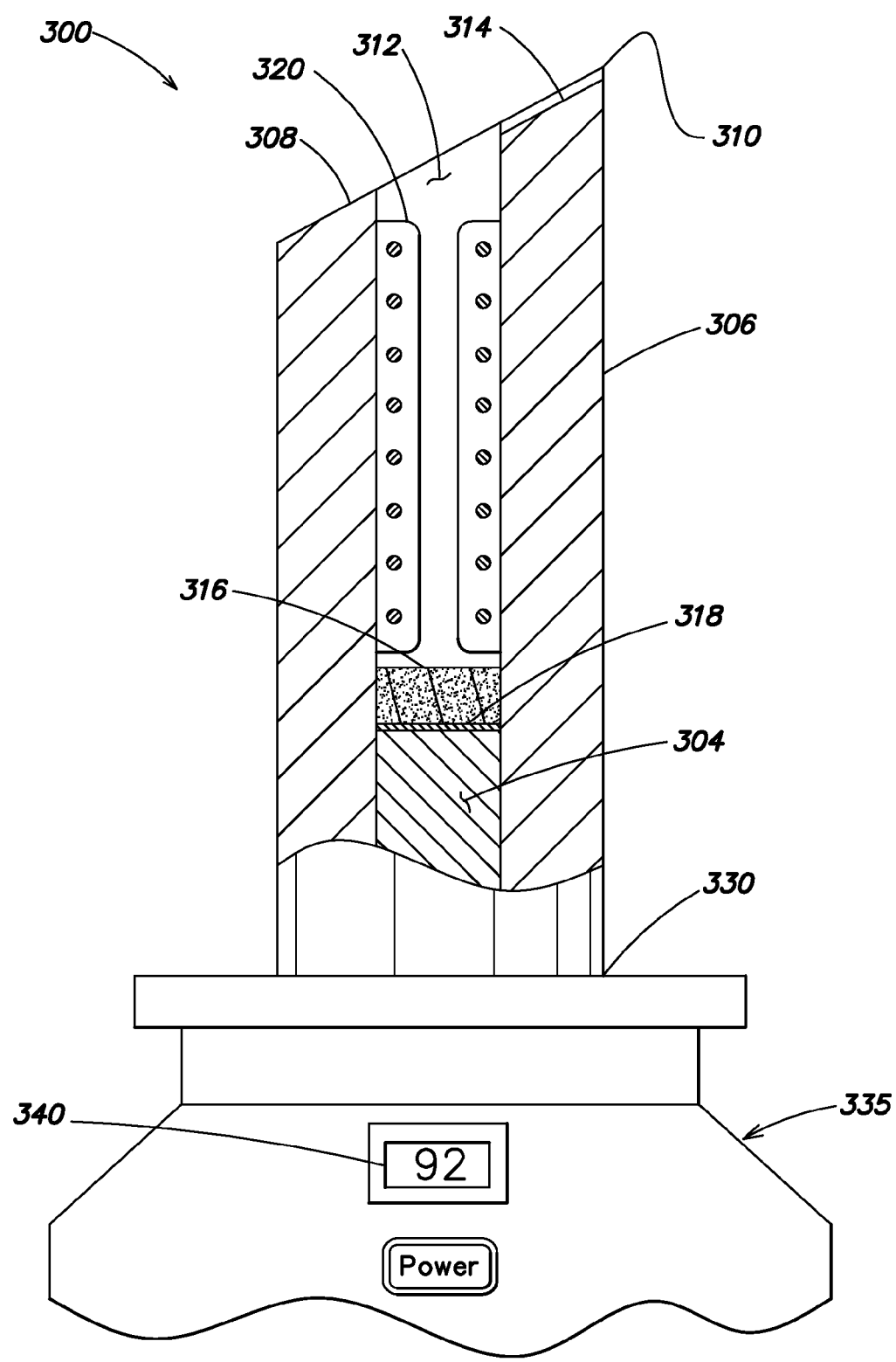
FIG. 3 is a partial cross-sectional view of an apparatus including another exemplary embodiment of an analyte sensor according to the present invention.

Again referring to FIG. 1A, an active region 116 may be positioned within the cavity 112, and preferably at the bottom of the cavity, thereby allowing exposure of the active region to the sample bio-fluid that enters the cavity 112 (e.g., by capillary action). The active region 116 may also be positioned in an abutting and/or electrical contacting relationship with a working electrode 118. The active region 116 may include one or more catalytic agents or reagents adapted to promote an electrochemical reaction between an analyte within the bio-fluid sample and the catalytic agents or reagents to produce reaction products and the flow of electrons. A portion of the working electrode 118 formed proximate to the core 104 may then channel the electron flow (e.g., through the core 104 and/or cladding 106) and provide an electrical current which may be proportional to the concentration of the analyte in the bio-fluid sample. This current may then be conditioned and displayed in any suitable readout form, such as in a digital readout of a test apparatus (e.g., such as shown in FIG. 3).

One group of catalytic agents useful within the active region 116 is the class of oxidase enzymes which includes, for example, glucose oxidase (which converts glucose), lactate oxidase (which converts lactate), and D-aspartate oxidase (which converts D-aspartate and D-glutamate). In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes which may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The active region 116 may include one or more layers (not explicitly shown) in which the catalytic agents (e.g., enzymes) and/or other reagents may be immobilized or deposited. The one or more layers may comprise various polymers, for example, including silicone-based or organic polymers such as polyvinylpyrrolidone, polyvinylalcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the active region 116 including, but not limited to, coupling the enzymes to the lattice of a polymer matrix such as a sol gel, cross-linking the agents to a suitable matrix such as glutaraldehyde, electropolymerization or electroactive polymers, and formation of an array between the enzymes via covalent binding, or the like.

In one or more embodiments, the working electrode 118 may be directly coupled to the active region 116. In some embodiments, a portion (e.g., an end surface or pocket) of the conductive core 104 in contact with the active region 116 may comprise the working electrode 118. In other embodiments, an electrochemically active layer (not explicitly shown) may be positioned adjacent to the end of the core 104 and/or cladding 106 to form the working electrode 118. The electrochemically active layer may include, for example, noble metals such as platinum, palladium, gold or rhodium, or other suitable materials. In a glucose detection embodiment, the active layer may undergo a redox reaction with hydrogen peroxide when polarized appropriately. The redox reaction causes an electrical current to be generated at the working electrode 118 by electron transfer that is proportional to the concentration of the analyte that has been converted into hydrogen peroxide. This current may be conveyed from the electrochemically active layer 116 through the core 104 and/or cladding 106 to a testing or measurement device (e.g., such as shown in FIG. 3).

Additionally, in some embodiments of the invention, mediators may be included in the active region 116 to promote the conversion of the analyte to detectable reaction products. Mediators comprise substances that act as intermediaries between the catalytic agent and the working electrode 118. For example, a mediator may promote electron transfer between the reaction center where catalytic breakdown of an analyte takes place and the working electrode 118, and may enhance electrochemical activity at the working electrode 118. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the working electrode 118.

The analyte sensor 100 may also include a reference electrode 120, which in one or more embodiments may also function as a counter electrode providing a return path for an electrical current. As described further with reference to FIGS. 1A to 10, the reference electrode may be arranged, formed and/or implemented in a number of different ways. In the embodiment depicted in FIG. 1A, the reference electrode 120 may comprise Ag/AgCl or other suitable electrically conductive materials such as carbon, and may be formed as a coil (as shown), foil, film or the like. In the depicted embodiment, the reference electrode 120 may be coupled to the sensor 100 and may be surrounded by a sealing material 122 such as a flexible polymer (e.g., polycarbonate, polyethylene) which may be concentric with, and surround, at least a portion of the cladding 106 of the sensor body 102. Confined within the sealing material 122 may be an electrolyte fluid 124 such as a viscous conductive liquid (e.g., a hydrogel) or other salt-containing solution. In some embodiments, the surface of the cladding 106 may include an insulating layer of a non-permeable polymer (e.g., polyimide, polystyrene) to prevent an electrical pathway between the electrolyte fluid 124 and the cladding 106.

To form an electrochemical cell, the reference electrode 120 may be coupled to the electrolyte fluid 124 contained in the sealing material 122. Likewise, the active region 116 of the cavity 112 may be fluidly coupled to the electrolyte fluid 124 in the sealing material 122 via a conduit 126. The surface area of the reference electrode 120 may be considerably larger than the surface area of the working electrode 118 to enhance conductivity, and in some embodiments, the surface area of the reference electrode 120 may be about 1000 times as large as a surface area of the working electrode 118 or larger. Other reference electrode sizes may also be used. An electrical circuit connection to the reference sensor electrode 120 may be made by any suitable means, such as a conductive strip (not shown) formed along a side of the sensor. Thus, a meter (M) may connect to the reference electrode 120 and the sensor body 102 and be used to read out an electrical current generated by the active region 116.

Figure 2:
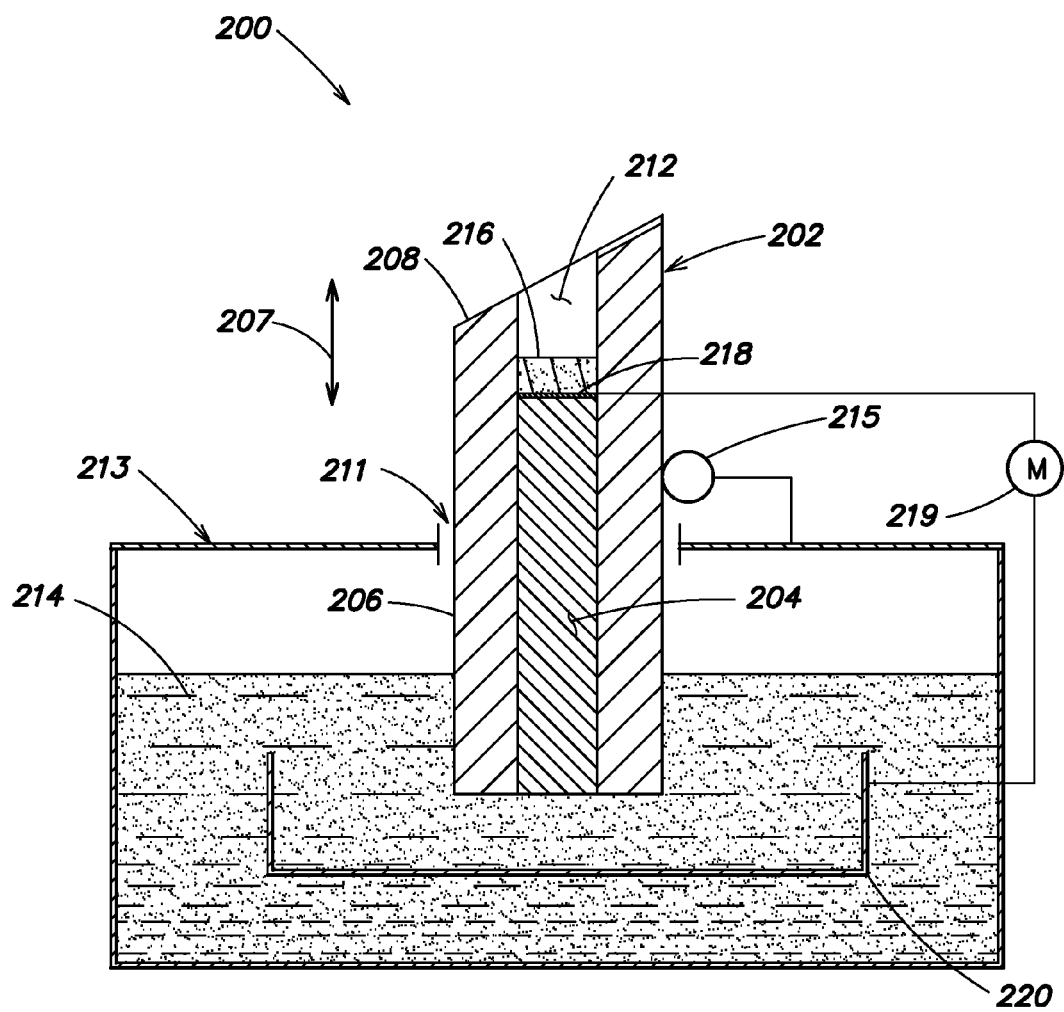
FIG. 2 is a cross-sectional view of an apparatus including another exemplary embodiment of an analyte sensor according to the present invention.

FIG. 2 is a cross-sectional view of a testing apparatus including another embodiment of a lancet analyte sensor 200 according to the present invention. In this embodiment, a sensor body 202, which may have similar features to the sensor body 102 described with respect to FIG. 1A above, is integral with, and movably coupled to, a housing 213. For example, the sensor body 202 may be extended forwardly and retracted backwardly through a port 211 in the housing 213 (as indicated by the line 207). In some embodiments, the sensor body 202 may be extended forwardly out of the housing 213 in order to insert the cleaved end 208 into the patient and collect a bio-fluid sample in the cavity 212, and thereafter may be retracted backwardly into the housing 213 for post-sample analysis (e.g., current measurements). The sensor body 202 may be coupled to any suitable motion producing mechanism. For example, a motive device 215 may cause relative movement between the housing 213 and sensor body 202. The motive device 215 may be a spring whose energy may be released with a trigger mechanism, for example, or an actuator such as a linear motor or solenoid, which is adapted to effectuate such linear movement (e.g., extension and retraction).

In some embodiments, the motive device 215 may be electrically coupled to a working electrode 218 of the sensor body 202, such that the motive device 215 receives an electrical signal when an analyte is detected in an active region 216 of the sensor 200 and a current is produced at the working electrode 218. In one or more embodiments, upon receipt of the current signal, the motive device 215 may cause the sensor body 202 to retract into the housing 213. The housing 213 may contain an electrolyte fluid 214 (an 'electrolyte') such as a salt-containing solution, a hydrogel, or the like.

In operation, the sensor 200 may be in fluid communication with the electrolyte 214 such that when the body 202 is retracted, the body 202 may be at least partially submerged in the electrolyte 214 within the housing 213. The housing 213 may include a reference electrode 220 (e.g., an Ag/AgCl coil or foil or another suitable electrically conductive reference electrode material) positioned within the electrolyte fluid 214 and coupled to the sensor 200. In this embodiment, electrochemical activity at the working electrode 218 of the sensor 200 may be communicated via a core 204 and/or cladding 206 to the electrolyte fluid 214 and to the reference electrode 220 when the body 202 is retracted into the housing 213 (e.g., upon detection of the analyte). A current measurement device 219, such as an ammeter (labeled "M"), may be coupled to the reference electrode 220 and working electrode 218 to measure the electrical activity representative of the analyte concentration in the active region 216 of the lancet analyte sensor 200.

FIG. 3 is a partial cross-sectional view of another embodiment of a lancet analyte sensor 300 according to the present invention. In the embodiment depicted in FIG. 3, a reference electrode 320 may be at least partially positioned in a cavity 312 of the lancet sensor 300 where the bio-fluid sample may be received. The electrode 320 may be affixed or otherwise coupled to the cladding 306, for example. In the illustrated embodiment, the reference electrode 320 may be configured as a coil (e.g., of Ag/AgCl or another suitable electrically conductive material). The cavity 312 may be enlarged to accommodate a length of the reference electrode 320.

In the illustrated embodiment, contact between the reference electrode 320 and an active region 316 and working electrode 318 of the lancet sensor 300 is avoided to ensure proper performance of the lancet sensor 300. This may be achieved, for example, by affixing the reference electrode 320 to an interior surface of the cavity 312 while maintaining the reference electrode 320 a clearance distance above the active region 316. A suitable electrical connection to the reference sensor may be made along a side of the sensor 300 (not shown). As in the prior embodiments, the sensor 300 may include a cleaved end 308 formed on the cladding 306 to form an integral lancet 310 and may similarly include a capillary channel 314. In the depicted embodiment, the lancet analyte sensor 300 is shown inserted into a port 330 of a testing apparatus 335. Upon insertion into the testing apparatus 335, an electrical contact comes into direct contact with the core 304 and/or cladding 306. Accordingly, an analyte level proportional to the current in the core 304 and/or cladding 306 may be determined and may be displayed on a suitable digital display 340, for example.

Figure 4:
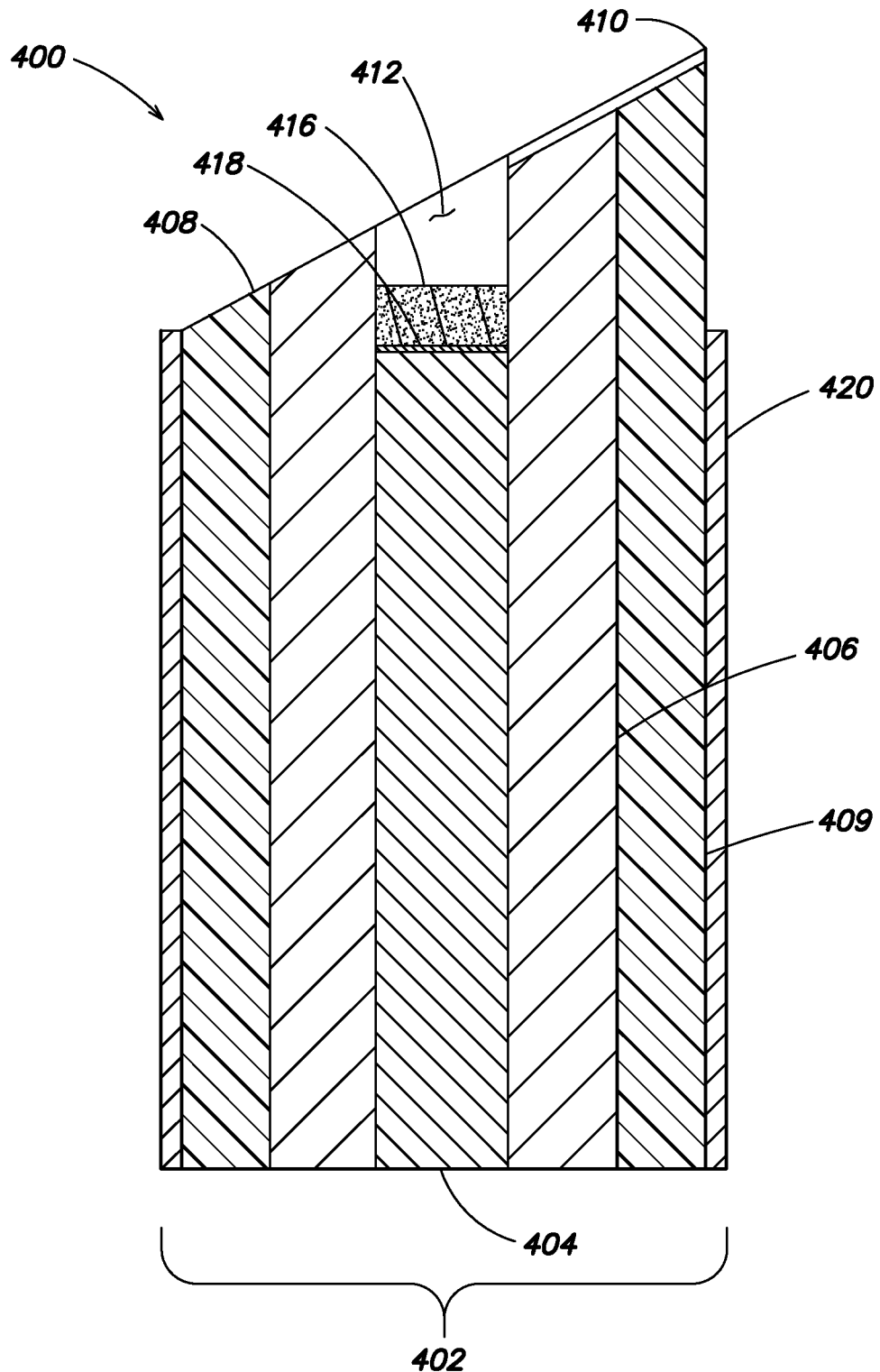
FIG. 4 is a cross-sectional view of another exemplary embodiment of an analyte sensor according to the present invention.

FIG. 4 is a cross-sectional view of another embodiment of a lancet analyte sensor 400 according to the present invention. The lancet sensor 400 may include a sensor body 402 including a core 404 including a conductive material surrounded by a cladding 406 including a semiconductor material. In the depicted embodiment, a cavity 412 may be formed in the cladding 406 and may be included proximate the core 404. A lancet 410 may be provided by forming a cleaved end 408 on the sensor 400 as in the previous embodiments. Additionally included in this embodiment may be an insulating layer 409 surrounding the cladding 406. In some embodiments, the core 404 may comprise carbon material (e.g., graphite) and the cladding 406 may comprise silicon carbide (SiC) although other materials may also be used (as described previously). The cladding 406 may further comprise a combination of silicon carbide and silicon nitride ($SiC/Si_3N_4$) and/or any other suitable semiconductor material.

The insulating layer 409 may comprise any suitable dielectric material, such as a polymer. The thickness of the insulating layer 409 should be between about 5 microns and about 100 microns, for example. Other thicknesses may be used. Surrounding the insulating layer 409 may be a reference electrode 420 of a conducting material such as Ag/AgCl or a noble metal (e.g., gold, silver, platinum, palladium or the like). A suitable thickness for the reference electrode 420 may be between about 10 microns and about 100 microns, for example. Some embodiments may include a thickness of the insulating layer 409 of between about 30 and 70 microns, and a thickness of the reference electrode 420 of between about 10 and 30 microns.

In one or more embodiments of the present invention, the lancet body 402 may be constructed by first removing carbon material from the core region near the cleaved end 408 of a SiC/C fiber by suitable techniques (as described above), to form the cavity 412 and then forming the insulating layer 409 over the cladding 406.

The cavity 412 may then have applied therein an active region 416. The active region 416 may include, as described in the previous embodiments, one or more catalytic agents adapted to promote an electrochemical reaction of the analyte into reaction products which produces electron flow in a working electrode 418 formed at an upper surface of the core 404 within the cavity 412. The core 404 may form a portion of the working electrode 418 with or without an additional active layer (e.g., platinum). Moreover, the cladding 406 may form a portion of the working electrode as well. By the inclusion of the insulating layer 409 surrounding the cladding 406, a reference electrode 420 may be coupled to the outer peripheral surface of the sensor 400 by placement directly in contact with the insulating layer 409, for example. The reference electrode 420 may be made from Ag/AgCl layer or strip, a platinum film, and/or other suitable electrically conductive materials.

Figure 5:
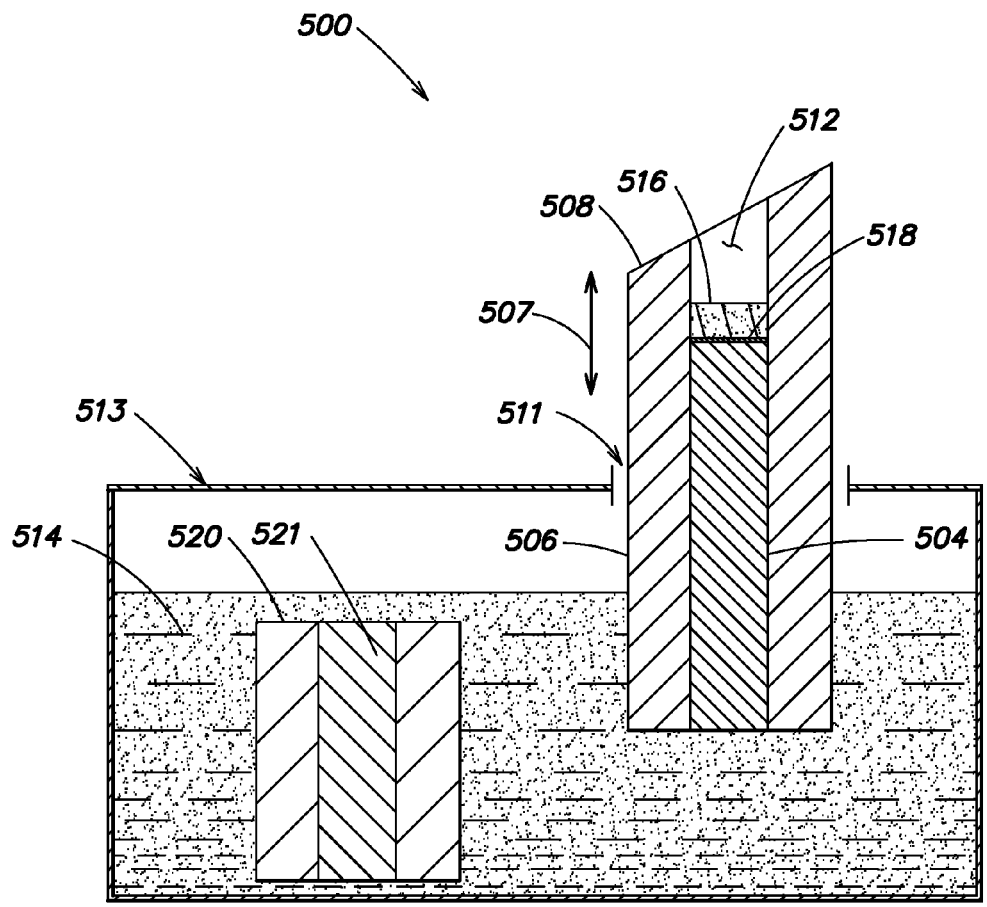
FIG. 5 is a cross-sectional view of an apparatus including another exemplary embodiment of an analyte sensor according to the present invention.

FIG. 5 is a cross-sectional view of another embodiment of a test apparatus including another embodiment of a lancet analyte sensor 500. In the depicted apparatus, the lancet analyte sensor 500 and the reference electrode 520 may be mounted in a housing 513. The housing 513 may contain an electrolytic fluid 514 such as a hydrogel, and the sensor 500 and the reference electrode 520 may be positioned within, and coupled to each other by, the electrolytic fluid 514. As in the embodiment of FIG. 2, the lancet analyte sensor 500 may be extendable through a port 511 in the housing 513 for the purposes of taking a bio-fluid sample, and then may be retractable back into the port 511 as illustrated by line 507. As the sensor 500 may be used for sample collection, it may have a cleaved end 508 formed on the cladding 506 as described above, while the reference electrode 520 need not be used for sample collection, and therefore it need not have a cleaved end. In accordance with its sampling function, the sensor 500 may have a cavity 512 for receiving a bio-fluid sample containing an analyte, an active region 516 coupled to the cavity 512 including one or more catalytic agents or reagents, and a working electrode 518 coupled to the active region 516. The working electrode 518 may comprise a portion of the core 504 and or cladding 506 of the sensor 500, such as the end surface, which is exposed to the active region 516.

In contrast, the reference electrode 520 need not have a cavity 512, and rather, the end of the conductive core 521 may be directly exposed to the electrolytic fluid 514 in the housing 513. The exposed core 521 may act as a reference electrode 520 adapted to detect charge carriers introduced into the electrolytic fluid 514 from the active region 516 of sensor 500 because of the sensor's contact with the fluid 514.

Figure 6:
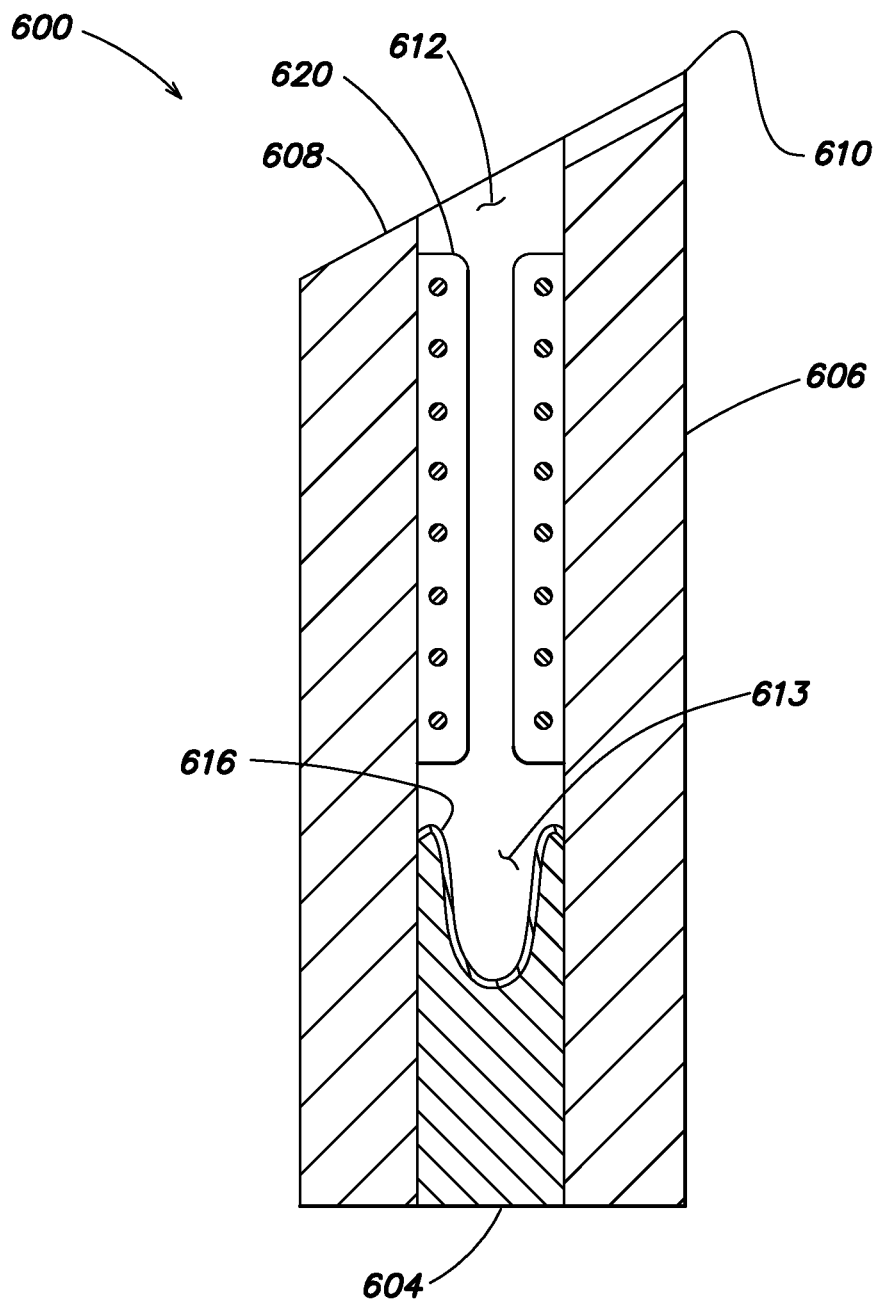
FIG. 6 is a cross-sectional view of additional exemplary embodiment of an analyte sensor according to the present invention.

FIG. 6 depicts a cross-sectional view of another embodiment of a lancet analyte sensor 600 according to the present invention. The lancet sensor 600 may comprise a core 604 of a conductive material surrounded by a cladding 606 of a semiconductor material wherein a cavity 612 may be formed in the cladding and included proximate the core 604. A lancet 610 may be provided by forming a cleaved end 608 on the sensor 600, as in the previous embodiments. The core 604 and the cladding 606 may be manufactured from the materials as described previously. A reference electrode 620 may be coupled to the sensor 600 such as by being provided in the cavity 612 for example, similarly as described with reference to FIG. 3. Other reference electrodes may be employed. In the depicted embodiment, the core 604 may further include a pocket 613 formed therein which may form part of the cavity 612. An active region 616 may be applied in the pocket 613. Because the pocket 613 may include a conductive material (e.g., graphite) along its sides, an effective contact area of the active region 616 in contact with the core 604 may be enlarged.

FIG. 7A and FIG. 7B depict cross-sectional and frontal views, respectively, of another embodiment of a lancet analyte sensor 700 according to the present invention. As in the previous embodiments, the lancet sensor 700 comprises a core 704 comprised of a conductive material which may be surrounded by a cladding 706 comprised of a semiconductor material. Similarly, a cavity 712 may be formed in the cladding 706 and may be provided proximate the core 704. A lancet 710 may be provided by forming a cleaved end 708 on the cladding 706 and core 704. The core 704 and the cladding 706 may be manufactured from the materials described previously. In the depicted embodiment, the cavity 712 may be formed in the cladding 706 and the hollowed out area may be defined by the side walls of the cladding 706. Optionally, a channel 714 may be provided along the side of the cladding 706 to aid in the flow of a bio-fluid sample into the cavity 712. An active region 716 may be positioned in the cavity 712. The cavity 712 may be any shape such as round, oval, or elongated, and may extend laterally from the surface of the cladding 706 to intersect with the core 704 at a bottom of the cavity 712. Providing the cavity 712 along a side surface of the lancet analyte sensor 700 may minimize blockage of the cavity 712 by perforated bio-material (e.g., skin) as compared to when the cavity is located at an end of the sensor. Additional cavities (not shown) may be provided along the side such that additional analytes may be tested.

FIG. 8 is a cross-sectional view of an additional embodiment of a lancet analyte sensor 800 according to the present invention. As in the previous embodiments, the lancet sensor 800 may comprise a sensor body 802 which may have a core 804 comprised of a conductive material surrounded by a cladding 806 comprised of a semiconductor material. Similar to the previous embodiments, a cavity 812 may be formed proximate the core 804. In the depicted embodiment, the cavity 812 may be at least partially formed by inner walls of a separate lancet member 817 which may be coupled to the sensor body 802 by a suitable coupler 821 (e.g., by a section of tubing). The lancet member 817 may include an end having a portion that is separated from the body 802 or cleaved at an angle thereby forming an enlarged portion in the cavity adjacent to the core 804. The enlarged portion may allow additional area for applying the active region 816. The lancet member 817 may be formed of a hollow SiC fiber or other tubing material, such as stainless steel (e.g., an austenitic stainless steel). An exemplary length of the lancet member 817 may be about 2 microns to about 5 microns, although other lengths may be used. A lancet 810 may be provided by forming a cleaved end 808 on the lancet member 817. In this embodiment, the core 804 and the cladding 806 may be manufactured from the same materials described previously. As in the previous embodiments, the active region 816 may be positioned in the cavity 812 in contact with the core 804. Although not shown, a reference sensor may be provided on the sensor body 802, for example.

The embodiment of FIG. 9 illustrates another embodiment of lancet analyte sensor 900 similar to the sensor of FIG. 8, except that it further includes a reference sensor 920 positioned at the end of, and coupled to, the sensor body 902. Additionally, in some embodiments, the coupler 921 include at least one vent hole 922.

Figure 10:
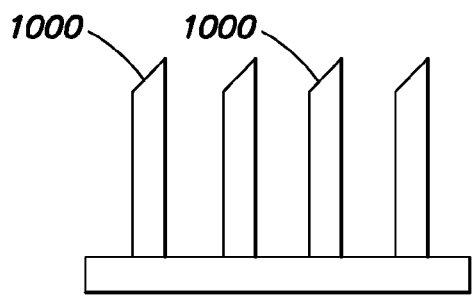
FIG. 10 is a frontal view of an apparatus including an array of analyte sensors according to the present invention.

FIG. 10 illustrates an apparatus including an array of sensors 1000. The sensors 1000 may be arranged in any configuration, such as in a row or in any three dimensional arrangement (e.g., in a random or ordered pattern). By including multiple sensors 1000 in an array, the overall signal level may be enhanced, such as for continuous monitoring, for example. Any of the embodiments of sensors previously described may be incorporated into the array, such as those described with reference to FIG. 1A through FIG. 9.

In another aspect, the present invention provides a method of manufacturing an analyte sensor, including providing a fiber comprised of a semiconductor material; forming a cavity proximate to the fiber, applying an active region in the cavity, and forming lancet on the analyte sensor.

Figure 11:
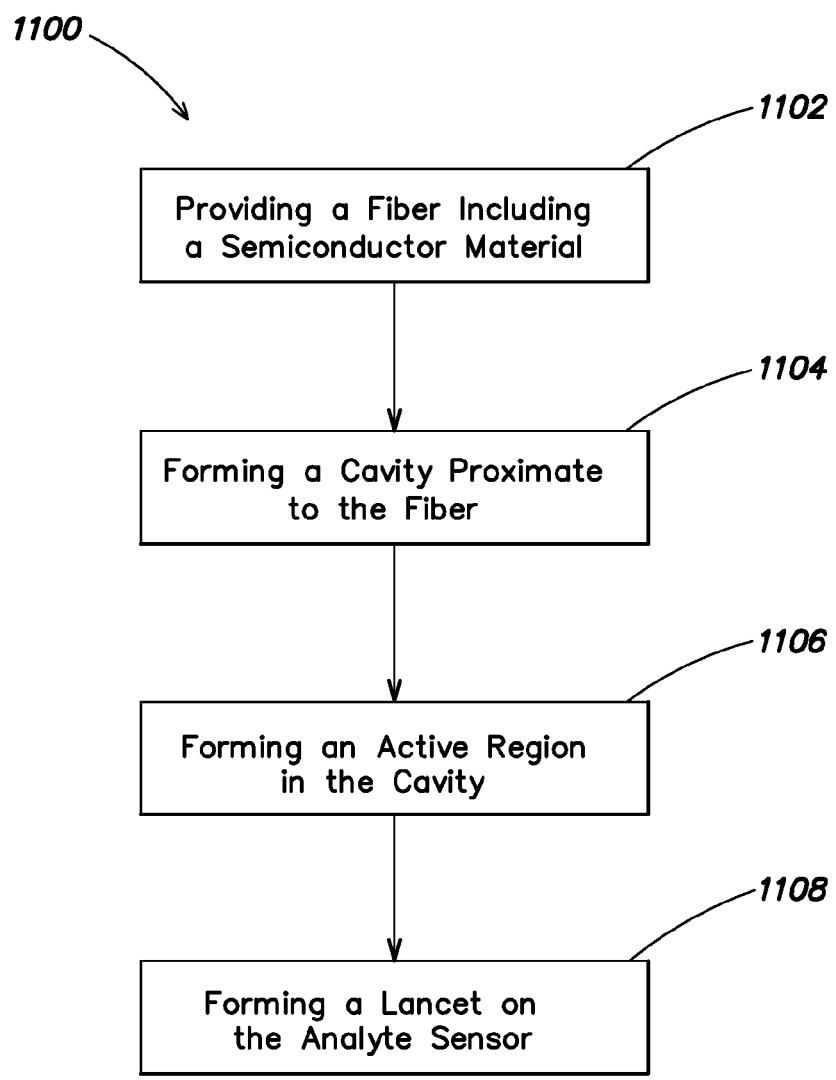
FIG. 11 is a flowchart illustrating a method of manufacturing lancet analyte sensors according to the present invention.

FIG. 11 illustrates a method of manufacturing an analyte sensor according to the present invention. The method 1100 includes a step 1102 wherein the fiber is provided including a semiconductor material. The fiber may be a SiC/C fiber as discussed above. The fiber is provided cut to the appropriate length. A cavity may then be formed proximate the fiber in step 1104. This may be by removal of a portion of the core, by the formation of a cavity in a side wall of the fiber, or by the attachment of a separate lancet member. An active region may be applied in contact with the fiber and in the cavity in step 1106 by methods described above. In step 1108, a lancet may be formed on the analyte sensor. Of course, the steps may not be provided in the order shown. For example, the step of lancet formation in step 1108 may take place during the cutting operation. Likewise, the step of forming a cavity in step 1104 may be accomplished after the application of the active region, for example by adding a separate lancet member. Similarly, the step of forming the active region in the cavity may not occur until the attachment of a separate lancet member.

The foregoing description discloses only exemplary embodiments of the invention. Modifications of the above disclosed analyte sensors and apparatus incorporating them, which fall within the scope of the invention, will be readily apparent to those of ordinary skill in the art. Accordingly, while the present invention has been disclosed in connection with exemplary embodiments thereof, it should be understood that other embodiments may fall within the spirit and scope of the invention, as defined by the following claims.

The invention claimed is:

1. An analyte sensor, comprising:
   a cylindrical sensor body comprised of a semiconductor material;
   an active region positioned within and coupled to the cylindrical sensor body, the active region configured to determine an analyte concentration level; and
   a cleaved surface on a leading end of the cylindrical sensor body forming a lancet on the analyte sensor;
   wherein at least a portion of the cylindrical sensor body is in contact with a fluid electrolyte.

2. The analyte sensor of claim 1, wherein the sensor body comprises a core of a conductive material and a cladding surrounding the core comprised of the semiconductor material.

3. The analyte sensor of claim 2, wherein the conductive material of the core comprises carbon and the semiconductor material of the cladding comprises silicon carbide.

4. The analyte sensor of claim 1, wherein the sensor body includes an end in electrical contact with the active region thereby forming at least a portion of a working electrode.

5. The analyte sensor of claim 1, wherein a cavity is located in the interior of the cylindrical sensor body, the active region being positioned within the cavity.

6. The analyte sensor of claim 1, wherein the lancet is formed on a cladding of the sensor body.

7. The analyte sensor of claim 6, further comprising a channel formed proximate the lancet adapted to direct a biofluid into the cavity.

8. The analyte sensor of claim 1, further comprising a reference electrode coupled to the analyte sensor.

9. The analyte sensor of claim 8, wherein the reference electrode is positioned in contact with a fluid electrolyte.

10. The analyte sensor of claim 9, further comprising a sealing material that surrounds at least a portion of the sensor body and that contains the fluid electrolyte.

11. The analyte sensor of claim 1, wherein the analyte sensor is further adapted to extend and retract within a port in a housing.

12. The analyte sensor of claim 1, further comprising an insulating layer surrounding the sensor body.

13. The analyte sensor of claim 1, wherein the lancet is formed on a separate lancet member coupled to the sensor body.

14. The analyte sensor of claim 1, further comprising a reference electrode at least partially surrounding a portion of the sensor body.

15. The analyte sensor of claim 1, wherein the analyte comprises one or more of glucose, lactate, aspartate, and glutamate.

16. The analyte sensor of claim 1, further comprising:
   a core comprised of a conductive material; a cladding comprised of the semiconductor material surrounding the core;
   a cavity formed proximate to the core; and
   the active region positioned within the cavity.

17. The analyte sensor of claim 1, further comprising:
   a fiber comprised of the semiconductor material; and
   the active region in contact with the fiber.

18. An analyte sensor comprising:
   a cylindrical sensor body comprised of a semiconductor material;
   an active region positioned within and coupled to the cylindrical sensor body, the active region configured to determine an analyte concentration level;

a cleaved surface on a leading end of the cylindrical sensor body forming a lancet on the analyte sensor; and a reference electrode coupled to the analyte sensor;

wherein the reference electrode comprises a coil, foil, or film.

19. An analyte sensor comprising:

a cylindrical sensor body comprised of a semiconductor material;

an active region positioned within and coupled to the cylindrical sensor body, the active region configured to determine an analyte concentration level;

a cleaved surface on a leading end of the cylindrical sensor body forming a lancet on the analyte sensor; and a cavity proximate to the active region and a reference electrode positioned within the cavity.

20. An analyte sensor comprising:

a cylindrical sensor body comprised of a semiconductor material;

an active region positioned within and coupled to the cylindrical sensor body, the active region configured to determine an analyte concentration level; and a cleaved surface on a leading end of the cylindrical sensor body forming a lancet on the analyte sensor;

wherein a cavity is formed into a side wall of the cylindrical sensor body.

21. The analyte sensor of claim 20, wherein the cavity includes a pocket formed into a core of the cylindrical sensor body.

* * * * *